(12) United States Patent
Chabrier De Lassauniere et al.

(10) Patent No.: US 9,006,274 B2
(45) Date of Patent: Apr. 14, 2015

(54) THIAZOLE DERIVATIVES FOR TREATING DYSKINESIAS CAUSED BY A CHEMICAL TREATMENT

(75) Inventors: Pierre-Etienne Chabrier De Lassauniere, Paris (FR); Michel Auguet, Palaiseau (FR); Brigitte Spinnewyn, Bures sur Yvette (FR)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 1582 days.

(21) Appl. No.: 11/995,092

(22) PCT Filed: Jul. 7, 2006

(86) PCT No.: PCT/FR2006/001638
§ 371 (c)(1),
(2), (4) Date: Jan. 8, 2008

(87) PCT Pub. No.: WO2007/006942
PCT Pub. Date: Jan. 18, 2007

(65) Prior Publication Data
US 2008/0207709 A1      Aug. 28, 2008

(30) Foreign Application Priority Data
Jul. 8, 2005 (FR) ..................................... 05 07303

(51) Int. Cl.
*A61K 31/426* (2006.01)
*A61K 31/427* (2006.01)

(52) U.S. Cl.
CPC ............ *A61K 31/427* (2013.01); *A61K 31/426* (2013.01)

(58) Field of Classification Search
None
See application file for complete search history.

(56) References Cited

U.S. PATENT DOCUMENTS

| | | | |
|---|---|---|---|
| 2004/0058909 A1* | 3/2004 | Goldstein ................ | 514/211.13 |
| 2005/0038087 A1* | 2/2005 | Chabrier De Lassauniere et al. ............................. | 514/365 |
| 2014/0018400 A1* | 1/2014 | Schmidt et al. ............... | 514/365 |

FOREIGN PATENT DOCUMENTS

| WO | WO 01/26656 A2 | 4/2001 |
|---|---|---|
| WO | WO 02/083656 A2 | 10/2002 |
| WO | WO 02/083656 A3 | 10/2002 |
| WO | WO 02/083863 | 10/2002 |
| WO | WO 2007/006941 | 1/2007 |
| WO | WO2007/006942 A1 | 1/2007 |

OTHER PUBLICATIONS

"Vitamin E, Lipids, and Lipid Peroxidation Products in Tardive Dyskinesia" by Brown et al., Biol. Psychiatry 43, 863-67 (1998).*

"Levodopa and dopamine agonists in the treatment of Parkinson's disease: advantages and disadvantages" by Ogawa, Eur. Neurol. 34(Suppl 3), 20-8 (1994).*
"Dyskinesia: L-dopa-induced and tardive dyskinesia" by Rascol et al., Clin. Neuropharmacol. 24, 313-23 (2001).*
"Neuroleptic-induced vacuous chewing movements as an animal model of tardive dyskinesia: a study in three rat strains" by Tamminga et al., Psychopharmacology 102, 474-78 (1990).*
International Preliminary Examination Report dated Sep. 28, 2007 with English Translation.
International Search report for PCT/FR2006/001638.
Written Opinion for PCT/FR2006/001638.
Lees, Andrew: "Alternatives to Levodopa in the Initial Treatment of Early Parkinson's Disease," Drugs and Aging, 2005 New Zealand, vol. 22, No. 9, pp. 731-740, Feb. 9, 2005 (XP009064944).
Heintz, R. et al.: "Pargyline reduces-prevents Neuroleptic-induced Acute Dystonia in Monkeys," Psychopharmacology, vol. 93, No. 2, pp. 207-213, 1987 (XP009064996).
Birkmayer W. et al.: "The Potentation of the Anti Akinetic Effect alter L-Dopa Treatment by an Inhibitor of Mao-B, Deprenil," Journal of Neural Transmissions, Springer Verlag, Vienna, at, vol. 36, pp. 303-326, 1975 (XP000575120).
Koe, B.K. et al.: "Mono Amine Oxidase Inhibitors Antagonize the Acceleration of Brain Dopamine Synthesis induced by Neuroleptic Drugs In-Vivo Implications for the Treatment of Tardive Dys Kinesia," Experientia (Basel), vol. 31, No. 6, pp. 669-671, 1975 (XP009065015).
Trebini, F. et al.: "Clinical Evaluation of Selegiline L. Deprenyl in the long-term L Dopa Treatment Syndrome," Acta Neurologica (Naples), vol. 40, No. 5, pp. 432-439, 1985 (XP009065047).
NIH National Institute of Neurological Disorders and Stroke, Restless Leg Syndrom Fact Sheet, retieved from the Internet at: http://ww.ninds.nih.gov/disorders/restless_legs/detail_restless_legs.htm?css=print (2001).
Grandas et al.; "Nocturnal problems occurring in Parkinson's disease," Neurology, vol. 63 (Suppl 3); pp. S8-S11; 2004.
Evers, Stefan et al.; "Genetic Association of Huntington's Disease and Restless Legs Syndrome? A Family Report," Movement Disorders, vol. 18, No. 2, pp. 225-227; 2003.
Glasauer; "Restless Legs Syndrome," Spinal Cord, vol. 39, pp. 125-133; 2001.

* cited by examiner

*Primary Examiner* — Theodore R West
(74) *Attorney, Agent, or Firm* — Hunton & Williams LLP

(57) ABSTRACT

The invention relates to the use of derivatives of thiazoles having general formula (I) for the preparation of a medicament for the treatment or prevention of dyskinesias caused by a chemical treatment. The invention also relates to a combination of thiazole derivatives having general formula (I) and at least one compound selected from among neuroleptics or products that act on the dopaminergic system for the treatment or prevention of dyskinesias caused by a chemical treatment.

(I)

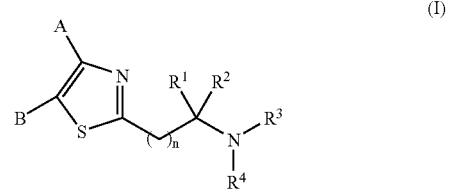

11 Claims, 2 Drawing Sheets

FIGURE 1
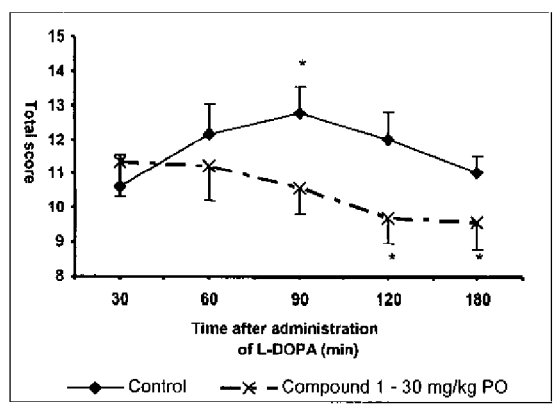
Figure 1a
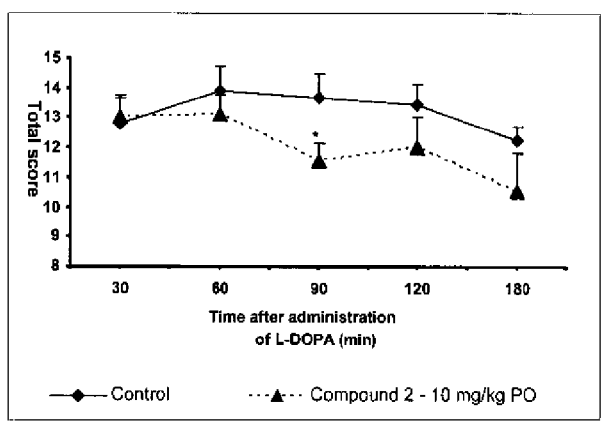
Figure 1b
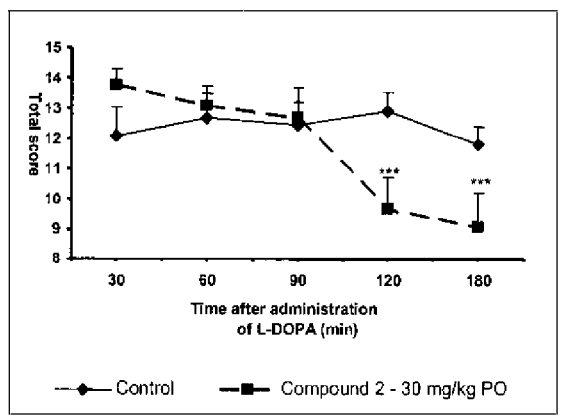
Figure 1c

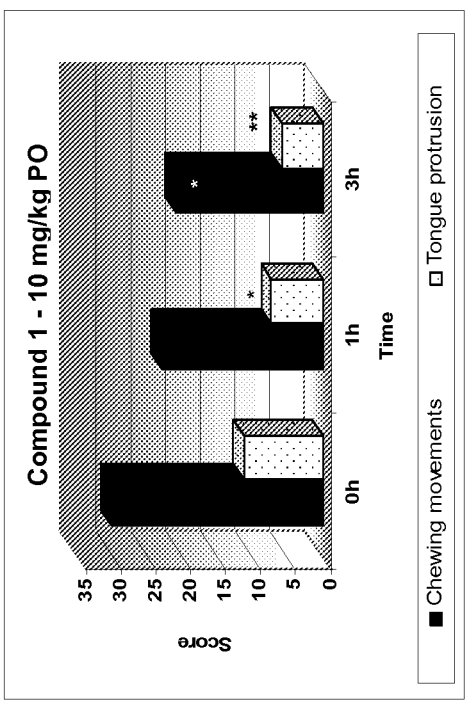
Figure: 2a
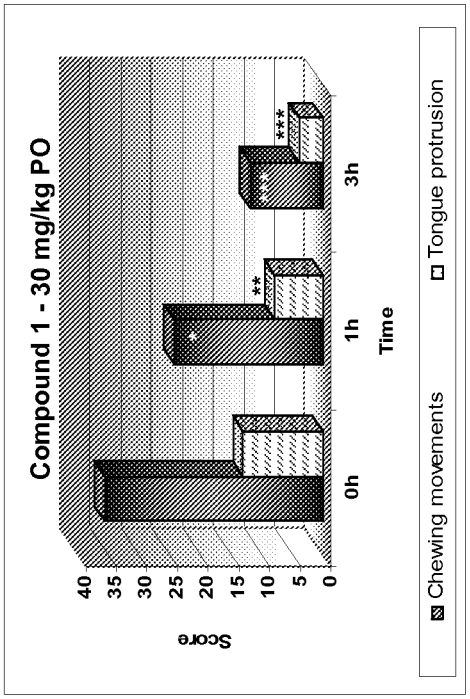
Figure: 2b
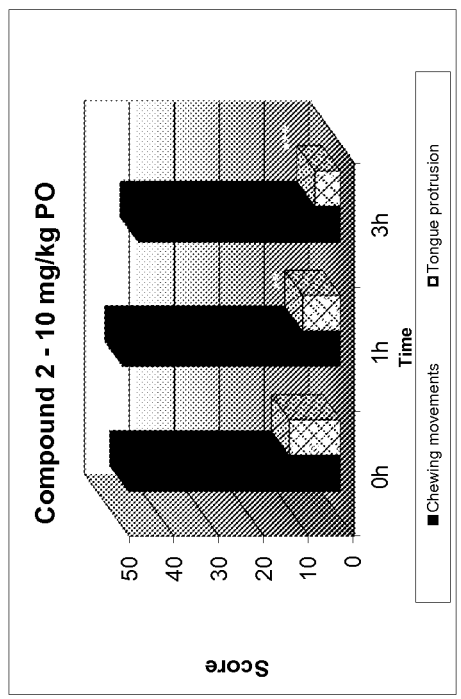
Figure: 2c
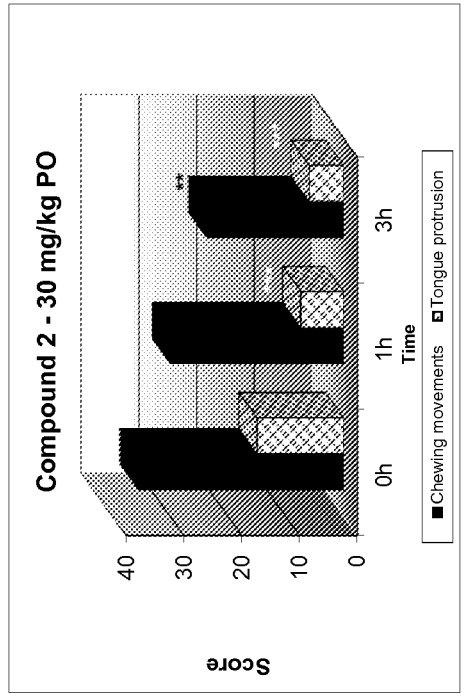
Figure: 2d

THIAZOLE DERIVATIVES FOR TREATING DYSKINESIAS CAUSED BY A CHEMICAL TREATMENT

CONTINUITY DATA

This application is a national stage application of PCT/FR2006/001638, filed on Jul. 7, 2006, which in turn claims priority to FR 0507303, filed on Jul. 8, 2005; both of which applications are hereby incorporated by reference in their entirety.

BACKGROUND OF INVENTION

1. Field of Invention

A subject of the present invention is thiazole derivatives of general formula (I) described below for preparing a medicament intended for treating or preventing dyskinesias caused by a chemical treatment.

2. Description of the Related Art

Dyskinesias are generally characterized by involuntary or abnormal movement disorders.

Among the dyskinesias, those caused by a chemical treatment are distinguished. In this case, within the meaning of the present invention, the terms induced dyskinesias or tardive dyskinesias are used, these 2 forms of dyskinesias being dyskinesias caused by a chemical treatment.

Induced dyskinesias: these are induced by a chemical treatment, such as for example in patients treated with L-Dopa which is a dopamine precursor. Patients treated with L-Dopa are generally Parkinsonians, i.e. individuals suffering from Parkinson's disease who present with a pathological deficit of Dopamine as the main characteristic of the disease. Treatment with dopatherapy is absolutely necessary for these patients in order to restore a sufficient level of endogenous dopamine. However, in a significant number of patients it causes severe side effects which are manifested by so-called induced dyskinesias, generally after several years of treatment with L-Dopa. This form of dyskinesia which is a serious undesirable iatrogenic effect of L-Dopa results in particular in the progressive emergence of involuntary movements, muscle rigidity and gait disorders. The emergence of this type of dyskinesia never occurs in "de novo" parkinsonian patients having never previously received treatment with L-Dopa. Unfortunately, at present no satisfactory treatment exists for dyskinesias induced by Dopatherapy. A clinician responsible for a parkinsonian suffering from dyskinesia induced by L-Dopa is then compelled to reduce the daily dose of L-Dopa in order to reduce the severity of the abnormal movements (dyskinesia), which is then accompanied by an aggravation of the blockage phenomena due to Parkinson's disease. The clinician and the patient then have to choose between 2 evils: blockages or dyskinesia.

At present no satisfactory medicinal treatments exist for dyskinesias induced by L-Dopa (a few compounds have been proposed, such as for example yohimbine, idazoxan or amantadine). Only surgical intervention by stimulation of the globus pallidus constitutes a therapeutic strategy which could be effective in the most severe cases, which is clearly not suitable for the majority of patients.

Tardive dyskinesias: these appear tardively in patients receiving long-term treatment with certain medicaments, in particular neuroleptics. By way of example these are patients suffering from schizophrenia treated with the typical neuroleptics (such as for example dopamine D2 receptor agonists) such as haloperidol, or so-called atypical agonists (dopamine D3 or D4 receptor ligands) such as clozapine or olanzepine. These treatments cause so-called tardive dyskinesias as side-effects. These are in particular abnormal involuntary movements, at the facial, oral, lingual, masticatory level, and diffuse movements, rhythmic swinging of the trunk, swaying and stamping;

Thus, the therapeutic treatments known at present are not satisfactory.

In order to respond to the needs of patients, it has become necessary to find a new means for treating these dyskinesias caused by a chemical treatment which are very incapacitating for patients.

Therefore the problem that the invention proposes to solve is to provide a novel compound suited to treating dyskinesias caused by a chemical treatment.

SUMMARY OF THE INVENTION

Unexpectedly, the Applicant has demonstrated that it is possible to use thiazole derivatives of general formula (I) described below for preparing a medicament intended for treating or preventing dyskinesias caused by a chemical treatment.

Yet more unexpectedly, the Applicant has demonstrated that the combination of the thiazole derivatives of general formula (I) described below and at least one compound chosen from the products acting on the dopaminergic system or neuroleptics makes it possible to treat or prevent dyskinesias caused by a chemical treatment.

Finally the use and the combination according to the invention have the advantage of being able to be utilized in patients and animals suffering from movement disorders.

The combination according to the invention has the advantage of avoiding the side-effects caused by a long-term therapeutic treatment.

Other advantages and characteristics of the invention will become clearly apparent on reading the description and the following examples which are given purely by way of illustration and are in no way limitative.

DETAILED DESCRIPTION OF THE PREFERRED EMBODIMENTS

A first subject of the invention is the use of a compound of general formula (I)

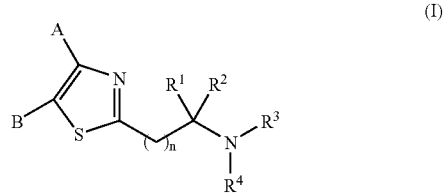

in the form of racemic, enantiomeric mixture or any combination of these forms, in which:

A1 represents a radical (A1)

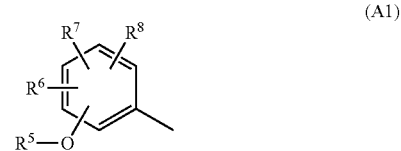

in which $R^5$ represents a hydrogen atom or an alkyl radical, $R^6$, $R^7$, $R^8$ represent independently a hydrogen atom or an alkyl, cycloalkyl, hydroxy or alkoxy radical;

B represents a hydrogen atom or an alkyl radical;
n represents an integer from 0 to 5;
R1 and R2 represent independently a hydrogen atom or an alkyl or cycloalkyl radical;
$R^3$ et $R^4$ represent independently a hydrogen atom or an alkyl radical, or $R^3$ and $R^4$ form together with the nitrogen atom which carries them a heterocycle comprising in total from 1 to 2 heteroatoms and from 5 to 7 members, a heterocycle the missing members of which are chosen from —$CH_2$—, —$NR^{14}$—, —O— or —S—, $R^{14}$ representing a hydrogen atom or an alkyl radical, or a —$COR^{15}$, —$COOR^{15}$ or —$CONR^{16}R^{17}$ radical, $R^{15}$ representing an alkyl radical and $R^{16}$ and $R^{17}$ represent independently a hydrogen atom or an alkyl radical, or a salt of general formula (I) defined above for preparing a medicament intended for treating or preventing dyskinesias caused by a chemical treatment.

Within the meaning of the present invention, by alkyl or alkoxy radical is meant, unless otherwise specified, a linear or branched alkyl or alkoxy radical containing 1 to 6 carbon atoms. By cycloalkyl radical, unless otherwise specified, is meant a cycloalkyl radical containing 3 to 7 carbon atoms.

Preferably, by linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals.

By pharmaceutically acceptable salt is meant in particular within the meaning of the invention addition salts of inorganic acid such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

Moreover, certain of the compounds of general formula (I) can be presented in the form of enantiomers. The present invention includes the two enantiomeric forms and all combinations of these forms, including the "R, S" racemic mixtures. In an effort to simplify matters, when no specific configuration is indicated in the structural formulae, it must be understood that the two enantiomeric forms and their mixtures are represented.

Preferably, the compounds according to the invention are such that the $R^5$ radical of A1 is a hydrogen atom.

Preferably, the compounds according to the invention are such that the $R^6$, $R^7$, $R^8$ radicals of A1 represent independently a hydrogen atom or an alkyl radical.

Preferably, the compounds according to the invention are such that n is comprised between 0 and 3, more preferentially in that n is equal to 0.

More preferentially, the compounds according to the invention are such that $R^1$ represents a hydrogen atom.

Still more preferentially, the compounds according to the invention are such that $R^2$ represents a hydrogen atom or an alkyl radical.

More particularly, the compounds according to the invention are such that $R^3$ or $R^4$ represents a hydrogen atom or an alkyl radical.

Still more particularly, the compounds according to the invention are such that they are the following compounds:
4-[2-(aminomethyl)-1,3-thiazol-4-yl]-2,6-di(tert-butyl)phenol;
4-{2-[(1R)-1-aminoethyl]-1,3-thiazol-4-yl}-2,6-di-tert-butylphenol
4-{2-[(1S)-1-aminoethyl]-1,3-thiazol-4-yl}-2,6-di-tert-butylphenol;

Preferably, the purpose of the invention is the use of a compound of general formula (I) or a salt of general formula (I) defined above for preparing a medicament intended for treating or preventing dyskinesias caused by a chemical treatment such as for example induced dyskinesia or tardive dyskinesia.

Preferentially, a subject of the invention is the use of a compound of general formula (I) or a salt of general formula (I) defined above for preparing a medicament intended for treating or preventing induced dyskinesias such as for example dyskinesias induced by levodopa (L-Dopa), by the levodopa-benzerazide combination or the levodopa-carbodopa combination, by pergolide, quinpirole, carbergoline, benzotropine, trihexylphenidyl, ropinorole, pramipexole and any other dopaminergic derivatives which are substituted for dopamine.

Preferentially, a subject of the invention is the use of a compound of general formula (I) or a salt of general formula (I) defined above for preparing a medicament intended for treating or preventing tardive dyskinesias such as for example tardive dyskinesias following treatment with phenothiazine derivatives, butyrophenone derivatives, haloperidol, risperidone, tetrabenazine derivatives, clozapine, olanzapine, fluoxetine, buspirone.

The use according to the invention does not relate to the treatment of dyskinesias not caused by a chemical treatment.

By dyskinesias not caused by a chemical treatment is meant within the meaning of the invention the abnormal pathological movements appearing as a clinical sign of a neurodegenerative disease.

The use according to the invention does not relate to the treatment of the abnormal pathological movements of Huntington's disease.

By dyskinesias caused by a chemical treatment is meant within the meaning of the invention dyskinesias which appear after administration of a chemical substance, which is at the origin of this dyskinesia (iatrogenic effect). In this case the dyskinesia caused by said chemical treatment is either a main pathology, or a side-effect of this chemical treatment. It should be noted that the dyskinesia caused following a chemical treatment, can appear during the administration of the compound or after stopping the treatment. A distinction can be made between mid-dose dyskinesias, or also those at the start or end of the dose.

A second subject of the invention is a combination of a compound of general formula (I) or a salt of general formula (I) defined above with one or more other chemical compounds, having or not having a therapeutic effect, in particular with a compound having a psychotropic effect.

Preferably, the combination according to the invention is a compound of general formula (I) or a salt of general formula (I) defined above and at least one compound chosen from the dopamine agonists, MAO inhibitors, catecholamine O-methyltransferase inhibitors or neuroleptics.

Among the dopamine agonists, there can be mentioned inter alia pergolide, bromocriptine or carbergoline, ropinirole or pramipexole.

More preferentially, the compound according to the invention of general formula (I) defined above or its salt can be used in combination with methyldopa or also L-Dopa.

Still more preferentially, the combination according to the invention is a compound of general formula (I) defined above or its salt and L-Dopa.

In particular, the invention relates to the combination of 4-[2-(aminomethyl)-1,3-thiazol-4-yl]-2,6-di(tert-butyl)phenol or its salt and L-Dopa.

In particular, the invention relates to the combination of 4-{2-[(1R)-1-aminoethyl]-1,3-thiazol-4-yl}-2,6-di-tert-butylphenol or its salt and L-Dopa.

In particular, the invention relates to the combination of 4-{2-[(1S)-1-aminoethyl]-1,3-thiazol-4-yl}-2,6-di-tert-butylphenol or its salt and L-Dopa.

The combination according to the invention is preferably a combined preparation for simultaneous or separate use or use spread over time in order to treat or prevent dyskinesias, in particular dyskinesias caused by a chemical treatment, in particular induced or tardive dyskinesias.

According to a variant of the use or of the combination according to the invention, it is possible to use or combine a decarboxylase inhibitor such as benserazide or carbidopa with the invention.

The compound of general formula (I) or its salt used according to the invention or the combination according to the invention can be in solid form, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The compound of general formula (I) or its salt used according to the invention or the combination according to the invention can also be presented in liquid form; for example, solutions, emulsions, suspensions or syrups. Appropriate liquid supports can be, for example, water, organic solvents such as glycerol or the glycols; similarly their mixtures, in varying proportions, in water.

The administration of a compound of general formula (I) or its salt used according to the invention or the combination according to the invention can be carried out for example by topical, oral, parenteral route, by intramuscular or sub-cutaneous injection. The administration dose can be comprised between 0.01 my and 10 g depending on the type of active ingredient used.

The following examples illustrate the invention without limiting its scope.

BRIEF DESCRIPTION OF THE SEVERAL VIEWS OF THE DRAWINGS

FIG. 1 represents the effect of the treatment with the compounds according to the invention on rats suffering from induced dyskinesia.

FIG. 2 represents the effect of the treatment with the compounds according to the invention on rats suffering from tardive dyskinesia.

EXAMPLES

The following compounds:
Compound 1: 4-[2-(aminomethyl)-1,3-thiazol-4-yl]-2,6-di(tert-butyl)phenol hydrochloride or dihydrochloride;
Compound 2: 4-{2-[(1R)-1-aminoethyl]-1,3-thiazol-4-yl}-2,6-di-tert-butylphenol hydrochloride
were subjected to the test for studying dyskinesias induced by L-DOPA in rats and to the test for studying tardive dyskinesias in rats following long-term treatment with a neuroleptic.

The synthesis of these compounds is described in the Application WO 01/26656.

Example 1

Study of Dyskinesias Induced by L-DOPA

Principle of the In Vivo Test (Experimental Model with Dyskinetic Rats):

An animal model is produced where the dyskinesia is induced in animals treated with L-Dopa (3-(3,4-dihydroxyphenyl)-L-alanine). First of all in order to cause a reduction in the level of endogenous dopamine at the level of the striatum, lesions are produced in the rats using 6-hydroxydopamine (6-OHDA). Following this injection of 6-OHDA, these animals become sensitive to the side-effects of L-dopa. In fact in order to remedy this endogenous dopamine deficiency, the rats receive an L-Dopa based treatment. However the treatment with L-Dopa causes a dyskinesia in the rat resulting from too greater quantities of exogenous L-Dopa which reach the brain and above all because of the lesions to the dopaminergic neurons which no longer regulate the endogenous dopamine level. The dyskinesia thus induced is evaluated by a statistical behaviour test.

Note: in order to improve the L-Dopa-based treatment, the latter is administered in combination with a decarboxylase inhibitor such as benserazide. In fact the L-Dopa passes through the hematoencephalic barrier with difficulty and therefore it can be decarboxylated at the peripheral level.

Measurement of Dyskinesias:

1/ Selection of Rats:

The study was carried out on young male rats. The rats are anaesthetized (chloral 400 mg/kg). Then they receive 2 stereotaxic injections of 6 µg of 6-hydroxydopamine in the left striatum using a 10 µl Hamilton microsyringe. The rats receive in fine 12 µg of 6-OHDA dissolved in 4 µl of 0.02% L-ascorbate. Four weeks later the lesion to the locus niger is produced in the rats. In order to quantify this lesion, an indirect measurement is used: the rotations induced by apomorphine (substance test). The animals receive a sub-cutaneous injection of 0.5 mg/kg of apomorphine and the right and left rotations of the animals are measured over 30 minutes. A net rotational asymmetry score is then determined. This score is expressed as the number of complete turns in the test cage/minute in the contralateral direction of the lesion.

The rats which exhibit an individual average greater than 4 complete turns/minute in the contralateral direction of the lesion are selected in order to carry out the in vivo test. This net rotational asymmetry score corresponds to animals the locus niger of which has significant lesions and which exhibit at least 90% dopamine depletion in the striatum (Lee et al.; 1996; Lundblad et al., 2002; Winkler et al., 1996).

2/ Induction of Dyskinesia in the Selected Rats:

Six weeks after the 6-hydroxydopamine (6-OHDA) lesions, the selected rats receive a daily intraperitoneal injection of L-Dopa methylester at a dose of 20 mg/kg and benserazide at a dose of 15 mg/kg. The injections take place from week 6 to week 9. From week 10, the rats receive a more concentrated dose: each day they receive an intraperitoneal injection of L-Dopa methylester at a dose of 25 mg/kg and benserazide at a dose of 15 mg/kg. From week 11, the rats receive two daily injections of L-Dopa methylester at a dose of 15 mg/kg and benserazide at a dose of 15 mg/kg. During week 11, the rats are evaluated 3 times per week for their level of abnormal and involuntary movements in order to determine whether the administered doses are sufficient to cause a dyskinesia in these animals. The rats are observed individually from 30 minutes to 180 minutes after injection of the L-Dopa; they are observed every 30 minutes. The movements which are observed at that time are considered to be dyskinetic movements when they meet the following criteria:
  the movements are induced by the L-Dopa;
  the movements affect the side of the body in the contralateral direction of the lesion;
  the movements are repetitive, involuntary and cannot be attributed to normal behaviour.

The abnormal and involuntary movements are classified in 4 sub-types:
  locomotive dyskinesia: increase in locomotion of the side contralateral to the lesion;
  axial dystonia: deviation of the posture of the neck and of the upper part of the body;
  oromandibular dyskinesia: stereotypical movements of the jaws and protrusion of the tongue;
  dyskinesia of the anterior limbs: repetitive and rhythmic jerking of the anterior limbs accompanied by a dystonic posture and/or strong grasping movements of the paws.

For each of these sub-types, the rats are marked on a scale of 0 to 4, knowing that:
  0=no movement,
  1=occasional movements,
  2=frequent movements,
  3=continuous movements but interrupted by a sensory distraction,
  4=continuous, acute movements, not interrupted by a sensory distraction.

The compounds according to the invention are tested in order to determine their ability to modulate the effects of the L-Dopa. For this purpose, the rats which exhibit a sufficient rate of abnormal and involuntary movements (rate greater than 2 for one observed movement and total rate greater than 8 for the 4 observed movements) are selected and continue to receive 2 to 4 injections/week of L-Dopa. After 12 to 14 weeks, the oral treatment with the compounds according to the invention to be tested starts and the rate of abnormal and involuntary movements is evaluated.

For each animal receiving a compound to be tested, another animal receives the solvent of the compound to be tested, generally water.

Results:
The rate of abnormal and involuntary movements is calculated statistically for each group of rats. The results are presented in FIG. 1 for compounds 1 and 2.

Compound 1 according to the invention is administered orally at a dose of 30 mg/kg to dyskinetic rats according to the protocol of Example 1 described above. The results presented were obtained with 9 tested animals.

Compound 2 according to the invention is administered orally at a dose of 10 and 30 mg/kg to dyskinetic rats according to the protocol of Example 1 described above. The results presented were obtained with 9 tested animals.

The score obtained makes it possible to evaluate the dyskinesia of the rat. The higher the numerical value of the score, the more dyskinetic the animal, with a maximum of 16 points.
  compound 1: at a dose of 30 mg/kg, the score is reduced from 11.3 to 9.6 after 180 minutes of treatment.
    At time 120 minutes after the administration of L-Dopa, the rats treated with compound 1 have a score of 10 points whilst the control (water) has a score of 12 points;
  Compound 2: at a dose of 30 mg/kg, the score is reduced from 13.8 to 9 points and at a dose of 10 mg/kg, the score is reduced from 13 to 10.6 points after 180 minutes of treatment.
    At time 120 minutes after the administration of L-Dopa, the rats treated with compound 2 (30 mg/kg) have a score of 9.7 points whereas the control (water) has a score of 12.9.

The results indicate a dose-dependent effectiveness of the treatment with Compounds 1 and 2 on the rats suffering from induced dyskinesia. This effectiveness is statistically significant. Compounds 1 and 2 do have an anti-dyskinetic effect.

Example 2

Study of Tardive Dyskinesia in Rats Treated with a Neuroleptic Over a Long Period Principle of the In Vivo Test (Experimental Model with Rats):
Tardive dyskinesia is a complication resulting from prolonged treatment with for example neuroleptics. It is characterized by repetitive, involuntary movements of the mouth, face and tongue. Long-term treatment with neuroleptics can lead to oromandibular dyskinesia, in particular it can lead to movements of mastication and protrusion of the tongue in rats. The principle of the test is to quantify the abnormal movements of the animals in a test cage during a determined time window (5 minutes).

Induction of Orofacial Dyskinesia in Rats:
A neuroleptic, haloperidol (originating from Sigma®), is administered over a long period to rats using an Alzet® osmotic pump. This osmotic pump (reference 2ML4 Alzet®) is filled with a solution of haloperidol at 10 mg/ml. This pump is implanted subcutaneously in rats weighing between 150 g and 160 g. After anaesthesia of the rats with isoflurane, a small incision is made in the skin at the level of the scapulae to allow insertion of the pump. Then the incision is sutured. The pump makes it possible to continuously administer haloperidol to the rats at a dose of 2 mg/kg/day for 28 days.

Measurement of Dyskinesia in Rats:
Between 21 to 28 days after the insertion of the pump, 12 rats are chosen at random for the test. 6 of them are treated with water (control), and the other 6 rats receive the compounds according to the invention.

Before the treatment (t=0) with the compounds to be tested, the rats are placed individually in plastic test cages. After a adaptation period of 2 minutes in the cage, the number of protrusions of the tongue and mastication movements is counted for 5 minutes. Then the treatment (compounds 1 and 2 to be tested) is administered orally at a dose of 2 ml/kg. Then the number of protrusions of the tongue and mastication movements is counted for 2 periods of 5 minutes each at t=1 hour and at t=3 hours after administration of the compound according to the invention.

Results:
The rate of protrusion of the tongue and mastication movements is calculated statistically for each group of rats. The results are presented in FIG. 2 *a* and *b* for Compound 1 and in FIG. 2 *c* and *d* for Compound 2.

Compounds 1 and 2 according to the invention are administered orally at a dose of 10 and 30 mg/kg to dyskinetic rats according to the protocol of Example 2 described above. The results presented were obtained with 8 tested animals.

The score obtained makes it possible to evaluate the dyskinesia of the rat. The higher the numerical value of the score, the more dyskinetic the animal.
  Compound 1: at a dose of 10 mg/kg, the score of chewing movements is reduced from 30.3 to 21. At a dose of 30 mg/kg, the score of chewing movements is reduced from 35.6 to 11.9.

Compound 2: at a dose of 10 mg/kg, the rate of protrusion of the tongue is significantly reduced after 3 hours, from 11.4 to 5. At a dose of 30 mg/kg, the number of mastication movements and the rate of protrusion of the tongue is significantly reduced after 3 hours, from 35.5 to 23.7 and from 15 to 6 respectively.

The results indicate a dose-dependent effectiveness of treatment with Compounds 1 and 2 on rats suffering from tardive dyskinesia and tardive orofacial dyskinesia caused by haloperidol. Compounds 1 and 2 do have an anti-dyskinetic effect.

The invention claimed is:

1. A method for treating a dyskinesia caused by a chemical treatment comprising administering to a patient in need thereof a compound of general formula (I)

(I)

wherein:

A represents (A1)

(A1)

wherein $R^5$ represents hydrogen or alkyl, $R^6$, $R^7$, and $R^8$ represent independently hydrogen, alkyl, cycloalkyl, hydroxy, or alkoxy;

B represents hydrogen or alkyl;

n represents an integer from 0 to 5;

$R^1$ and $R^2$ represent independently hydrogen, alkyl, or cycloalkyl;

$R^3$ and $R^4$ represent independently hydrogen, alkyl or $R^3$ and $R^4$ form together with the nitrogen atom to which they are attached a heterocycle comprising 1 to 2 heteroatoms and 5 to 7 members, wherein the members of the heterocycle include —$CH_2$—, —$NR^{14}$—, —O— or —S—, $R^{14}$ representing a hydrogen, alkyl, —$COR^{15}$, —$COOR^{15}$, or —$CONR^{16}R^{17}$, $R^{15}$ representing alkyl and $R^{16}$ and $R^{17}$ represent independently hydrogen or alkyl;

or of a salt of general formula (I) defined above, wherein the compound of general formula (I) is the only active ingredient for treating the dyskinesia.

2. The method of claim 1, wherein $R^5$ is hydrogen.

3. The method of claim 1, wherein $R^6$, $R^7$, and $R^8$ represent independently hydrogen or alkyl.

4. The method of claim 1, wherein n is between 0 and 3.

5. The method of claim 1, wherein n is equal to 0.

6. The method of claim 1, wherein $R^1$ represents hydrogen.

7. The method of claim 1, wherein $R^2$ represents hydrogen or alkyl.

8. The method of claim 1, wherein $R^3$ or $R^4$ represents hydrogen or alkyl.

9. The method of claim 1, wherein the method treats induced dyskinesia or tardive dyskinesia.

10. The method of claim 1, wherein the method treats a dyskinesia caused by levodopa (L-Dopa), levodopa-benzerazide combination, levodopa-carbodopa combination, pergolide, quinpirole, carbergoline, benzotropine, trihexylphenidyl, ropinirole, or pramipexole.

11. The method of claim 1, wherein the compound is:
4-[2-(aminomethyl)-1,3-thizol-4-yl]-2,6-di(tert-butyl) phenyl;
4-{2-[(1R)-1-aminoethyl]-1,3-thiazol-4-yl}-2,6-di-tert-butylphenol; or
4-{2-[(1S)-1-aminoethyl]-1,3-thiazol-4-yl}-2,6-di-tert-butylphenol.

* * * * *